United States Patent [19]

Markovich et al.

[11] Patent Number: 6,124,121
[45] Date of Patent: Sep. 26, 2000

[54] METHOD FOR PRODUCING L-LEUCINE

[75] Inventors: Gusyatiner Mikhail Markovich; Lunts Maria Grigorievna; Ivanovskaya Lirina Valerievna; Rostova Yulia Georgievna; Bachina Tatiana Aleksandrovna; Akhverdyan Valery Zavenovich; Khurges Evgeny Moiseevich; Livshits Vitaly Arkadievich; Kozlov Yuly Ivanovich; Debabov Vladimir Georgievich, all of Moscow, Russian Federation

[73] Assignee: Ajinomoto Co., Inc., Tokyo, Japan

[21] Appl. No.: 09/179,186

[22] Filed: Oct. 27, 1998

[30] Foreign Application Priority Data

Oct. 29, 1997 [RU] Russian Federation .......... N97117875

[51] Int. Cl.⁷ ....................................................... C12P 13/06
[52] U.S. Cl. .......................................... 435/116; 435/252.1
[58] Field of Search .................................... 435/116, 252.1

[56] References Cited

U.S. PATENT DOCUMENTS 3,970,519 7/1976 Tsuchida et al. .

FOREIGN PATENT DOCUMENTS 0 530 803 3/1993 European Pat. Off. .
0 698 668 2/1996 European Pat. Off. .

OTHER PUBLICATIONS

D.H. Calhoun, Journal of Bacteriology, vol. 126, No. 1, pp. 56–63, "Threonine Deaminase from *Escherichia coli*: Feedback–Hypersensitive Enzyme from a Genetic Regulatory Mutant", Apr., 1976.

*Primary Examiner*—Herbert J. Lilling
*Attorney, Agent, or Firm*—Oblon, Spivak, McClelland, Maier & Neustadt, P.C.

[57] ABSTRACT

L-leucine is produced by culturing a bacterium belonging to the genus Escherichia, which has an ability to produce L-leucine and is resistant to L-leucine in a culture medium to produce and accumulate L-leucine in the medium, and recovering L-leucine from the medium.

3 Claims, No Drawings

METHOD FOR PRODUCING L-LEUCINE

TECHNICAL FIELD

The present invention relates to a method for producing L-leucine, especially for a method for producing L-leucine using a bacterium belonging to the genus Escherichia. L-leucine is an essential amino acid which can be used as a nutritious additive for food or feed, reagents or materials for medical treatment, pharmaceutical or chemical industry, or a growth factor used for production of other amino acids such as lysine.

BACKGROUND ART

In the past, L-leucine have been produced by a method of fermentation primarily using microorganisms belonging to the genus Brevibacterium, Corynebacterium or Serratia or mutants thereof which produce L-leucine (Amino acid fermentation, JAPAN SCIENTIFIC SOCIETY'S PRESS, pp.397–422, 1986).

The highest level of L-leucine accumulation was obtained when using Brevibacterium flavum VKPM B2736: this strain produces L-leucine at a concentration up to 26 g/L on sucrose-containing media for 72 h of fermentation in a laboratory fermenter (USSR Author Certificate 1394711). And *Brevibacterium lactofermentum* 34 produces L-leucine up to 34 g/L on a medium with glucose (Appl. Environ. Microbiol., 51, p.1024 (1986)).

As described above, the productivity of L-leucine has been improved to some extent, however, the development of a more efficient and cost-effective method for producing L-leucine is required in order to meet increasing demand for L-leucine in the future.

On the other hand, microorganisms belonging to the genus Escherichia is potentially utilized as a potent L-leucine-producing bacteria due to its rapid growth rate, prominent data obtained from genetic analysis and plentiful genetic materials. However, there are few reports which disclose the production of L-leucine using bacteria belonging to the genus Escherichia.

As L-leucine-producing bacterial strains of the genus Escherichia, strain which is resistant to β-thienylalanine, strain which is resistant to β-thienylalanine and β-hydroxyleucine (Japanese Patent Publication No.62-34397 for two) and a strain which is resistant to 4-azaleucine or 5,5,5-trifluoroleucine (Japanese Laid-Open Publication No. 8-70879) are known.

However, there has been known neither L-leucine-resistant bacteria belonging to the genus Escherichia nor a relation between L-leucine resistance and a productivity of L-leucine.

DISCLOSURE OF THE INVENTION

The present invention has been made from the aforementioned viewpoint, an object of which is to improve a productivity of L-leucine of bacterium belonging to the genus Escherichia and to provide an efficient and cost-effective method for producing L-leucine.

As a result of diligent investigation in order to achieve the aforementioned object, the present inventors have found that conferring L-leucine resistance to a bacterium belonging to the genus Escherichia improves the productivity of L-leucine, and completed the present invention.

Namely, the present invention provides a bacterium belonging to the genus Escherichia, which has an ability to produce L-leucine and is resistant to L-leucine.

In another aspect, the present invention provides the aforementioned bacterium, which is further resistant to leucine analog(s). The leucine analog is exemplified by 4-azaleucine, 3-hydroxyleucine, β-thienylalanine and 5,5,5-trifluoroleucine and the like, preferably by 4-azaleucine and 3-hydroxyleucine.

In still another aspect, the present invention provides a bacterium belonging to the genus Escherichia, which is obtained by selecting a strain which is resistant to L-leucine and leucine analog(s) from bacteria belonging to the genus Escherichia, wherein said selection is performed at least once for each of L-leucine and leucine analog(s).

In still further aspect, the present invention provides a method for producing L-leucine, comprising the steps of:

culturing a bacterium according to any of claims 2 to 4 in a culture medium to produce and accumulate L-leucine in the medium, and recovering L-leucine from the medium.

The present invention will be explained in detail below.

<1> Bacterium belonging to the genus Escherichia of the present invention

A bacterium of the present invention is the bacterium belonging to the genus Escherichia, which has an ability to produce L-leucine and is resistant to L-leucine. As the bacterium belonging to the genus Escherichia, there may be exemplified by *Escherichia coli* (*E. coli*) A bacterium belonging to the genus Escherichia which has an ability to produce L-leucine is exemplified, for example, by bacteria having a resistance to leucine analog such as β-2thienylalanine, 3-hydroxyleucine, 4-azaleucine and 5,5,5-trifluoroleucine, which are described in Japanese Patent Publication No. 62-34397 and Japanese Patent Laid-Open Publication No. 8-70879, and by bacterium which can be bred by genetic engineering techniques as described in WO96/06926. The bacterium belonging to the genus Escherichia of the present invention can be obtained by selecting a strain which is resistant to L-leucine from bacteria belonging to the genus Escherichia having an ability to produce L-leucine. Alternatively, the bacterium belonging to the genus Escherichia of the present invention can be also obtained by selecting a strain which has an ability to produce L-leucine from bacteria belonging to the genus Escherichia being resistant to L-leucine. The most preferred embodiment of the bacterium belonging to the genus Escherichia, which is further resistant to leucine analog(s).

In a bacterium belonging to the genus Escherichia, L-leucine is synthesized through biosynthetic pathway inherent to L-leucine which diverges from the final intermediate (2-ketoisovalerate) of L-valine biosynthesis system. In a bacterium belonging to the genus Escherichia, the final step of L-valine biosynthesis and biosynthesis inherent to L-leucine are carried out by a group of enzymes encoded by ilvGMEDA operon and those encoded by leuABCD operon, respectively.

The leuABCD operon includes leuA, leuB, leuC and leuD genes. Among them, leuA encodes α-isopropylmalate synthase, leuB encodes β-isopropylmalate dehydrogenase, leuC and leuD encodes α-isopropylmalate isomerase. Of these enzymes, α-isopropylmalate synthase catalyzes the synthetic reaction from α-ketoisovalerate to α-isopropylmalate, α-isopropylmalate isomerase catalyzes the isomerization reaction from α-isopropylmalate to β-isopropylmalate and β-isopropylmalate dehydrogenase catalyzes the dehydrogenation reaction from β-isopropylmalate to α-ketoisocaproic acid which is the final intermediate of L-leucine biosynthesis. The amination reaction from α-ketoisocaproic acid to the final product, L-leucine, is mainly catalyzed by transaminase. Bacterium belonging to the genus Escherichia possess four kinds of transaminases, namely, transaminase A (aspartate-glutamate aminotransferase) encoded by aspC gene, transaminase B (BCAA aminotransferase) encoded by ilvE gene which is included in ilvGMEDA operon, transaminase C (alanine-valine aminotransferase) encoded by avtA gene and transaminase D (tyrosine aminotransferase) encoded by tyrB gene. These enzymes participate in various amination reactions. Of these enzymes, transaminase B and transaminase D catalyze the above-mentioned amination reaction from α-ketoisocaproic acid to L-leucine. Transaminase C and transaminase D catalyze the final step of L-valine biosynthetic pathway, which includes a common pathway among the L-valine biosynthesis and L-leucine biosynthesis.

Of above-mentioned reactions in the L-leucine biosynthetic pathway, the rate determining step is the synthetic reaction from α-ketoisovalerate to α-isopropylmalate catalyzed by α-isopropylmalate synthase which suffers feedback inhibition by L-leucine. Also, the expression of leuABCD operon is repressed by L-leucine. Expression of ilvBN gene encoding acetohydroxy acid synthase I suffers concerted repression by L-valine and L-leucine, expression of ilvGM gene encoding acetohydroxy acid synthase II suffers concerted repression by L-isoleucine, L-valine and L-leucine, and expression of ilvIH gene encoding acetohydroxy acid synthase III suffers repression by L-leucine.

α-Isopropylmalate synthase which is inhibited as well as leuABCD operon which is repressed only concern the biosynthesis of L-leucine. Therefore the above inhibition and repression do not cause cutting the route for supplying any nutrient substance, even if there exists an excess amount of L-leucine. Furthermore, although expression of ilvIH gene is repressed, expression of ilvBN gene and ilvGM gene encoding the other isozymes do not be effected. Therefore, it is thought that the presence of an excess amount of L-leucine does not effect the growth of cells, however the present inventor unexpectedly discovered that cell growth was inhibited under the presence of an excess amount of L-leucine. Furthermore, the present inventor succeeded in improving the L-leucine productivity of a bacterium belonging to the genus Escherichia by conferring the L-leucine resistance.

The method of obtaining bacteria belonging to the genus Escherichia which have L-leucine resistance and bacteria belonging to the genus Escherichia which have resistance to leucine analog will be explained below.

The bacteria belonging to the genus Escherichia which have L-leucine resistance can be obtained by culturing bacteria belonging to the genus Escherichia in a minimal medium containing L-leucine at the concentration that causes growth inhibition. Growth inhibition herein refers to slow growth or stop of growth. The selection of the mutants may be performed once or more. A concentration of L-leucine in the medium is not especially limited, but it is exemplified by 1 g/L or more, preferably 1 g/L–20 g/L. The bacteria belonging to the genus Escherichia may be subjected to a mutation treatment prior to the selection. Mutation may be performed by ultraviolet irradiation or by treatment with mutagen usually used for artificial mutagenesis such as N-methyl-N'-nitro-N-nitrosoguanidine (NTG) or nitrous acid and the like.

The bacteria belonging to the genus Escherichia which have L-leucine resistance, obtained as mentioned above, can grow in the presence of L-leucine at such a concentration that their parent strain cannot grow.

As mentioned above, L-leucine concerned with several regulation steps on L-leucine biosynthesis. Therefore, single mutation which causes L-leucine resistance may be effective for L-leucine productivity, however, it is preferably that more regulations are desensitized by double or more mutations. A bacterium belonging to the genus Escherichia which has single mutation can be used as starting source for breeding of L-leucine producing strain, even though its productivity of L-leucine is low.

The bacteria belonging to the genus Escherichia which have resistance to leucine analog can be obtained by culturing bacteria belonging to the genus Escherichia in a minimal medium containing leucine analog at the growth inhibitory concentration and selecting growing strains. The leucine analog is exemplified by 4-azaleucine, 3-hydroxyleucine, α-thienylalanine and 5,5,5-trifluoroleucine and the like, preferably by 4-azaleucine and 3-hydroxyleucine.

The selection of leucine-analog-resistant mutants may be performed with one kind of leucine analog, alternatively with more kinds of leucine analogs. The selection of the mutants may be performed once or more for one kind of leucine analog.

An amount of leucine analog which is to be added to the medium depends on a kind of leucine analog, but preferably ranges 0.1 g/L or more in the case of 4-azaleucine or 3-hydroxyleucine. The bacteria belonging to the genus Escherichia may be subjected to a mutation treatment prior to the selection in the same manner as described above.

In the case of selecting bacteria belonging to the genus Escherichia which have leucine-analog-resistance as well as leucine resistance, any order of selection for each of resistance is acceptable and the order is not restricted.

In the case of using *E. coli* K-12 or its derivatives as the bacterium belonging to the genus Escherichia, it is preferable to confer L-valine resistance in addition to L-leucine and/or L-leucine analog. K-12 strain does not express an active isozyme II of acetohydroxy acid synthase because a frameshift mutation exists in ilvG gene encoding a large subunit of the isozyme II which is one of acetohydroxy acid synthase isozymes of branched-chain amino acids biosynthetic pathway (Proc. Natl. Acad. Sci. USA 78, 922–925, 1981). The isozyme II does not suffer feedback inhibition by L-valine, however other isozymes, isozyme I and isozyme III, suffer feedback inhibition by L-valine. Therefore, K-12 strain cannot grow in a minimal medium in existence of excessive amount of L-valine, because biosynthesis of L-isoleucine, L-valine and L-leucine is inhibited. Consequently, to obtain a L-leucine producing strain derived from K-12 strain, it is preferable to use a strain having a reverse mutation of ilvG gene in which the frame is restored so as to recover the activity of the acetohydroxy acid synthase. Such a strain having a reverse mutation of ilvG gene will expresses L-valine resistance (Proc.Natl.Acad.Sci.USA 78,922–925, 1981). K-12 strain which has a resistance to L-valine can be obtained by culturing the strain in a minimal medium containing L-valine and selecting growing strains in the same manner as for L-leucine resistance or leucine analog resistance.

However, it is not required to confer L-valine resistance to a bacterium belonging to the genus Escherichia unlike the case of the K-12 strain described above, in the case of using a bacterium which belonging to the genus Escherichia which possesses acetohydroxy acid synthase which is not suffer from feedback inhibition by L-valine for breeding a bacterium which belonging to the genus Escherichia having L-leucine resistance.

The bacterium belonging to the genus Escherichia of the present invention may be enhanced in activity of one or more enzymes of L-leucine biosynthetic pathway by usual mutation treatment or genetic engineering techniques. Such an enhancement of the activity of the enzyme may be performed by introduction of recombinant DNA which is obtained by inserting a DNA fragment having an entire or a partial ilvGMEDA operon and/or leuABCD operon into a plasmid, phage or transposon to a bacterium belonging to the genus Escherichia.

The analysis of the nucleotide sequence of leuABCD operon was described in Nucleic Acid Res., 20, 3305–3308 (1992). The entire sequence of leuABCD operon has been registered in the database (DDBJ accession no. D10483, internet address of DDBJ: http://www.ddbj.nig.ac.jp). A DNA fragment having leuABCD operon can be obtained by amplifying the DNA fragment in accordance with PCR (polymerase chain reaction, refer to White, T. J. et al., Trends Genet., 5,185 (1989)) in which oligonucleotides prepared on the basis of the above described sequences are used as primers and chromosomal DNA of a bacterium belonging to the genus Escherichia is used as template for PCR. Alternatively, leuABCD operon can also be obtained by screening a chromosomal DNA library of a bacterium belonging to the genus Escherichia in accordance with hybridization by using an oligonucleotide probe prepared on the basis of the above described sequences.

The entire nucleotide sequence of ilvGMEDA operon and the nucleotide sequence of upstream region of the operon are described in Nucleic Acid Res., 15, 21372155 (1987) and Gene, 97, 21–27 (1991), respectively. A DNA fragment having ilvGMEDA operon can be obtained by PCR or hybridization using oligonucleotide probe or primers prepared on the basis of the above described sequence. Incidentally, in the case of using Escherichia coli K-12 or its derivative to obtain ilvGMEDA operon, it is preferable to use a strain having a reverse mutation of ilvG gene in which the frame is restored so as to recover the activity of the acetohydroxy acid synthase. The methods for obtaining ilvGMEDA operon and the method for amplifying the operon in a cell of a bacterium belonging to the genus Escherichia are fully described in WO96/06926 and Fr 2627508, respectively.

<2> Method for producing L-leucine

L-leucine can be efficiently produced by cultivating the bacterium which can be obtained as described above in a culture medium, producing and accumulating L-leucine in the medium, and recovering L-leucine from the medium.

In the method of present invention, the cultivation of the bacterium belonging to the genus Escherichia, the collection and purification of L-leucine from the liquid medium may be performed in a manner similar to the conventional fermentation method by which L-leucine is produced using a bacterium. A medium used in culture may be either a synthetic medium or a natural medium, so long as the medium includes a carbon and a nitrogen source and minerals and, if necessary, a suitable amount of nutrients which the bacterium used requires for growth. The carbon source may include one or more of various carbohydrates such as glucose and sucrose, and various organic acids. Regarding the mode of assimilation of the used bacterium, alcohol including ethanol and glycerol may be used. As the nitrogen source, it is possible to use various ammonium salts such as ammonia and ammonium sulfate, other nitrogen compounds such as amines, a natural nitrogen source such as peptone, soybean hydrolyte or digested fermentative microbe. As minerals, potassium phosphate, magnesium sulfate, sodium chloride, ferrous sulfate, manganese sulfate, or calcium carbonate may be used.

The cultivation is performed preferably under aerobic conditions such as a shaking culture, and an aeration and stirring culture, at a temperature of 20–40° C., preferably between 30 and 38° C. The pH of the culture is usually between 5 and 9, preferably between 6.5 and 7.2. The pH of the culture can be adjusted with ammonia, calcium carbonate, various acids, various bases, and buffers. Usually, cultivation for 1 to 3 days leads to the accumulation of the target L-leucine in the liquid medium.

After cultivation, insoluble substances such as cells are removed from the liquid medium by centrifugation and membrane filtration, and then the target L-leucine can be collected and purified by ionexchange, concentration and precipitation.

A bacterium belonging to the genus Escherichia of the present invention can be utilized as L-leucine producing strain or starting source for breeding of L-leucine producing strain. The present invention make it possible to produces L-leucine more efficiently in comparison with a formerly known method of producing L-leucine using a bacterium belonging to the genus Escherichia.

BEST MODE FOR CARRYING OUT THE INVENTION

The present invention will be more concretely explained below with reference to Examples.

EXAMPLE 1

Construction of the L-leucine Resistant Strains of *Escherichia coli*

<1> Selection of L-leucine resistant strains

The strains of Escherichia coli having L-leucine resistance and leucine analog resistance were constructed from the standard laboratory wild-type strain *E. coli* K-12 by stepwise selection as described below. The mutant strain having each resistance was obtained by selecting spontaneous mutants having the resistance. Concretely, *E. coli* K-12 or its mutant strain which was to be selected was plated on agar plate including L-leucine or leucine analog(s) at various concentrations indicated below. Then, the grown strain was selected.

At first, a mutant strain which was resistant to 5 g/L of L-valine was selected from *E. coli* K-12 prior to selection of the strain having L-leucine resistance and leucine analog resistance and obtained the strain B-5 (Val$^r$). From the strain B-5, a mutant strain which was resistant to 1 g/L of L-leucine was selected and designated as No.325 (Val$^r$, Leu$^r$). Then, a mutant strain which was resistant to 0.1 g/L of 4-aza-D,L-leucine (hereinafter referred to as "4-azaleucine") was selected from the strain No.325 and obtained the strain No. 244 (Val$^r$, Leu$^r$, AL$_r$). From the strain No. 244, a strain which was resistant to 2 g/L of 4-azaleuicine was selected and obtained the strain No. 70 (Val$^r$, Leu$^r$, AL$^{rr}$). The symbol, "Valr", "Leu$^r$" or "AL$^{rr}$" represents the strain which was conferred resistance to L-valine, L-leucine or azaleucine, respectively. The symbol, AL$^{rr}$ represents the strain which was conferred azaleucine resistance twice.

<2> The relationship between the resistance to L-leucine and L-leucine production To examine the relationship between the L-leucine resistance and L-leucine production, the spontaneous mutant strains resistant to 15 g/L of L-leucine from the strain No.70 which was obtained as described above.

Seven colonies isolated at random from the strain No. 70 and 10 mutants isolated at random from the L-leucine resistant mutants which were derived from the strain No. 70 were examined for L-leucine production. As a result, any of the leucine resistant mutants derived from the strain No.70 were more productive than the parent strain. The increase in production was 60% on the average.

EXAMPLE 2

Breeding of L-leucine Producing Strains from *Escherichia coli* K-12

The L-leucine producing strains were constructed by stepwise selection of strains which had resistance to L-valine, azaleuicine, hydroxyleucine and L-leucine from *E. coli* K-12 as described below. Concretely, *E. coli* strains which were to be selected were plated on agar plate including L-valine, leucine analog or L-leucine at various concentrations indicated as follows. Then, the grown strain was selected.

A mutant strain which was resistant to 5 g/L of L-valine was selected from *E. coli* K-12 and obtained the strain No. 101 (Val$^r$), which did not produce L-leucine. From the strain No. 101, a mutant strain which was resistant to 1.3 g/L of azaleucine. The obtained strain, No. 51 (Var$^r$, AL$^r$), produced about 0.05–0.1 g/L of L-leucine. Then, a strain having a resistance to 2 g/L of 3-hydroxy-D,L-leucine (hereinafter referred to as hydroxyleucine) was selected from the strain No. 51 and obtained the strain No.4 (Var$^r$, AL$^r$, Hleu$^r$). The symbol, "Hleu$^r$" represents the strain which was conferred hydroxyleucine resistance. The strain No. 4 produced more leucine (about 0.4–0.6 g/L).

The strain No. 4 was treated with NTG and mutants having resistance to 15 g/L of L-leucine were selected. As a result, two mutant strains, No. 57 and No. 103 (Var$^r$, AL$^r$, Hleu$^r$, Leu$^r$) were obtained. The leucine production by those mutants reached 1.5–1.7 g/L.

Among above strains, No. 4 (*Escherichia coli* K-12,4), No. 57 (*Escherichia coli* K-12,57) and No. 103 (*Escherichia coli* K-12,103) have been deposited in Russian National Collection of Industrial Microorganisms (Russia 113545 Moscow 1 Dorozhny proezd, 1) based on Budapest Treaty under the accession numbers of VKPM-7387, VKPM-7386 and VKPM7388, respectively.

EXAMPLE 3

The Production of L-leucine by the Strains No 57. and No. 103

Cells of the strains No. 57 and No. 103 were grown for 30 hours at 37° C. on M9 agar plates. Each loopful of cultures was inoculated into a shaker flask (250 ml), containing 15 ml of fermentation medium, containing (%) glucose (6), ammonium sulfate (1.5), potassium hydrophosphate (0.15), magnesium sulfate (0.1), thiamine (0.00001), calcium carbonate (2). The cultivation was carried out for 48 hours at 32° C. on rotary shaker (250 rpm). The L-leucine production by the strain No. 57 was 1.5 g/L, by the strain No. 103 was 1.7 g/L.

What is claimed is:

1. A bacterium belonging to the genus Escherichia, which has an ability to produce L-leucine and is resistant to L-leucine and leucine analogue(s), wherein said bacterium can grow in a medium containing 15 g/L of L-leucine.

2. The bacterium defined in claim 1, said leucine analog is selected from the group consisting of 4-azaleucine and 3-hydroxyleucine.

3. A method for producing L-leucine, comprising the steps of:

culturing a bacterium according to claim 1 or 2 in a culture medium to produce and accumulate L-leucine in the medium, and recovering L-leucine from the medium.

* * * * *